United States Patent
Bruce et al.

(10) Patent No.: US 9,770,549 B2
(45) Date of Patent: Sep. 26, 2017

(54) REUSABLE DATA STORAGE FIXTURES FOR USE WITH POWER INJECTOR SYRINGE ASSEMBLIES

(75) Inventors: John K. Bruce, Burlington, KY (US); Chad M. Gibson, Westerville, OH (US); Geoffrey S. Strobl, Williamsburg, OH (US)

(73) Assignee: LIEBEL-FLARSHEIM COMPANY LLC, Cincinnati, OH (US)

( * ) Notice: Subject to any disclaimer, the term of this patent is extended or adjusted under 35 U.S.C. 154(b) by 33 days.

(21) Appl. No.: 13/260,575

(22) PCT Filed: Apr. 5, 2010

(86) PCT No.: PCT/US2010/029888
§ 371 (c)(1),
(2), (4) Date: Sep. 27, 2011

(87) PCT Pub. No.: WO2010/117918
PCT Pub. Date: Oct. 14, 2010

(65) Prior Publication Data
US 2012/0035472 A1    Feb. 9, 2012

Related U.S. Application Data

(60) Provisional application No. 61/167,548, filed on Apr. 8, 2009.

(51) Int. Cl.
*A61M 5/31*    (2006.01)
*A61M 5/145*    (2006.01)
(Continued)

(52) U.S. Cl.
CPC ........ *A61M 5/14546* (2013.01); *A61M 5/007* (2013.01); *A61B 6/548* (2013.01);
(Continued)

(58) Field of Classification Search
CPC .... A61M 2005/14553; A61M 2209/04; A61M 2205/6054; A61M 5/007; A61M 5/14546; A61B 6/548
See application file for complete search history.

(56) References Cited

U.S. PATENT DOCUMENTS

| | | | | | |
|---|---|---|---|---|---|
| 5,187,843 | A | * | 2/1993 | Lynch | 24/587.12 |
| 5,505,230 | A | * | 4/1996 | Bartholomew | 138/164 |
| 2002/0038392 | A1 | | 3/2002 | De La Huerga | |
| 2002/0054940 | A1 | * | 5/2002 | Grose | A22B 7/007 426/231 |

(Continued)

FOREIGN PATENT DOCUMENTS

| | | |
|---|---|---|
| EP | 1433456 | 6/2004 |
| EP | 1723977 | 11/2006 |

(Continued)

*Primary Examiner* — Ruth S Smith
(74) *Attorney, Agent, or Firm* — Marsh Fischmann & Breyfogle LLP

(57) ABSTRACT

Systems and methods are presented for delivering medical fluids to a patient. A data storage device (120) is either separately attached to or incorporated within the structure of a reusable fixture that may be detachably connected to a barrel (111) of a syringe (107). A filling station (110) and an power injector (108) may each include a read-write device (114, 122) that is operable to read the data storage device (120) within its field of view. When the read-write devices (114, 122) are attached to the filing station (110) and the power injector (40), respectively, and when the fixture including the data storage device (120) is attached to the syringe (107), the read-write devices (114, 122) may be operable to store data on and read data from the data storage device (120) associated with the syringe (107). After an injection procedure, the fixture may be detached from the syringe (107) and reused with a new or resterilized syringe (107).

23 Claims, 13 Drawing Sheets

(51) Int. Cl.
*A61M 5/00* (2006.01)
*A61B 6/00* (2006.01)
(52) U.S. Cl.
CPC ............ *A61M 2005/14553* (2013.01); *A61M 2205/6054* (2013.01); *A61M 2209/04* (2013.01)

(56) References Cited

U.S. PATENT DOCUMENTS

| | | |
|---|---|---|
| 2003/0065287 A1 | 4/2003 | Spohn et al. |
| 2003/0173408 A1* | 9/2003 | Mosher et al. ............... 235/492 |
| 2004/0064041 A1* | 4/2004 | Lazzaro ............ A61M 5/14546 600/432 |
| 2004/0158205 A1* | 8/2004 | Savage ......................... 604/151 |
| 2005/0023431 A1 | 2/2005 | Coffelt |
| 2005/0240441 A1* | 10/2005 | Suzuki et al. .................... 705/2 |
| 2006/0186210 A1* | 8/2006 | Tethrake et al. .............. 235/492 |
| 2006/0214791 A1 | 9/2006 | Tethrake et al. |
| 2008/0122633 A1 | 5/2008 | Tetiyevsky |
| 2008/0131362 A1 | 6/2008 | Rousso et al. |
| 2009/0131756 A1* | 5/2009 | Nemoto ........................ 600/300 |

FOREIGN PATENT DOCUMENTS

| | | | |
|---|---|---|---|
| EP | 1782853 | 5/2007 | |
| EP | 1820524 | 8/2007 | |
| EP | 2000161 | 12/2008 | |
| WO | 9965548 | 12/1999 | |
| WO | 2006029105 | 3/2006 | |
| WO | WO 2006059597 A1 * | 6/2006 | ........ A61M 5/14546 |
| WO | 2006124775 | 11/2006 | |

* cited by examiner

REUSABLE DATA STORAGE FIXTURES FOR USE WITH POWER INJECTOR SYRINGE ASSEMBLIES

RELATED APPLICATIONS

This application is a U.S. National Stage of PCT/US2010/029888, filed 5 Apr. 2010, which claims priority to and is a non-provisional application U.S. Provisional Patent Application No. 61/167,548 filed on 8 Apr. 2009 entitled "MEDICAL FLUID DELIVERY SYSTEM WITH REUSABLE RFD FIXTURE". Priority is claimed to each patent application set forth in this Related Applications section.

FIELD OF THE INVENTION

The present invention generally relates to medical fluid delivery systems and, more particularly, to tracking/managing information related to such medical fluid delivery systems.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

Radio frequency identification ("RFID") tags are becoming more popular in various applications. RFID tags have been addressed in relation to medical applications, and specifically in relation to power injectors. For instance, RFID tags have been attached to power injector syringes and encoded with at least certain medical information. In many cases, power injector syringes are disposable (i.e., designed for only a single injection), and therefore, the entire syringe, including any associated RFID tag, is disposed of after use.

SUMMARY

As used herein, the phrase "fluidly interconnected" or the like refers to two or more components or entities being connected (directly or indirectly) in a manner such that fluid can flow (e.g., unidirectionally or bidirectionally) in a predetermined flow path therebetween. For example, "a conduit fluidly interconnected with a syringe" describes a configuration where fluid can flow from the syringe through any interconnecting devices (e.g., tubing, connectors) and into the conduit.

As used herein, the phrase "detachably mounted," "detachably interconnected," "detachably connected," or the like describes a relationship between components where the components are interconnected, yet retain the ability to be detached from each other where, after detaching, each of the components remains in a usable condition. For example, "a sleeve incorporating a data storage device and that is detachably mounted to a syringe" describes a condition where the sleeve is currently mounted to the syringe in a manner that allows for the sleeve to be detached from the syringe. Furthermore, after such detaching, both the sleeve and the syringe remain in a usable condition. For instance, the sleeve could be reattached to another syringe, and then also detached therefrom some time later.

As used herein, the term "field of view" when used in relation to a data reader denotes a region proximate to the data reader where a data storage device in that region will be readable by the data reader.

As used herein, an "operator" may be any appropriate person who may participate in the process of injecting fluid into a patient. Accordingly, an operator may include an imaging technician, nurse, doctor, and/or any other appropriate medical personnel.

A first aspect of the present invention is embodied by a power injector syringe assembly that includes a syringe barrel, a plunger, a fixture that is detachably connected to the syringe barrel, and a data storage device on the fixture. The plunger is movable relative to the syringe barrel and includes a plunger head that is disposed within the syringe barrel.

A number of feature refinements and additional features are applicable to the first aspect of the present invention. These feature refinements and additional features may be used individually or in any combination. As such, each of the following features that will be discussed may be, but are not required to be, used with any other feature or combination of features of the first aspect. The following discussion is applicable to the first aspect, up to the start of the discussion of a second aspect of the present invention.

The plunger and the syringe barrel of the power injector syringe assembly may be in the form of a pre-filled syringe in which the syringe barrel is pre-filled at a first location with an appropriate medical fluid to be discharged by the power injector and transported (e.g., in bulk with other prefilled syringes) to a second location in a common shipping container. In any case the syringe may be disposable (i.e., used for only one injection procedure), but in some instances, the syringe may be reused after any required sterilization.

The data storage device may be of any appropriate size, shape, configuration and/or type, including, for example, an RFID tag, a barcode, a magnetic stripe, and/or any other appropriate type of data storage technology. The data storage device may store data such as fluid type, concentration, manufacture date and/or lot, date filled, volume filled, expiration date, patient identification or medical information, injection protocol information, and the like. Further, the data storage device may be separately attached to the fixture in any appropriate manner, including adhering or otherwise anchoring the data storage device to an external surface of the fixture. Alternatively, the data storage device may be incorporated into the structure of the fixture itself. For example, in one embodiment, the data storage device may be embedded into the structure of the fixture during the manufacturing process (e.g., an injection molding process).

The fixture may be characterized as being separately installable on each of a plurality of syringes. The fixture may be installed on one syringe, removed from this syringe, and then installed on another syringe. The fixture may be characterized as including a connective structure, where this connective structure is of a configuration that allows the fixture to be installed on the syringe, and where this connective structure is of a configuration so as to remain in tact when the fixture is removed from one syringe such that the fixture may be installed on a different syringe using this same connective structure.

The fixture may be of any appropriate size, shape, configuration, and/or type to accommodate a data storage device and to detachably connect to the syringe barrel in a manner that allows the fixture to be repeatedly attached to and detached from a syringe barrel. In addition, the fixture may be disposable or reusable as appropriate. Moreover, the fixture may extend about a portion or an entirety of a perimeter of the syringe barrel, and may be used to structurally reinforce and/or support at least part of the syringe barrel when the syringe barrel is subjected to high pressures during an injection procedure. That is, the fixture may act in a secondary capacity as a pressure sleeve to reduce the potential for rupturing the syringe barrel when a power injector advances the plunger during an injection procedure, which may cause a significant pressure to develop within the syringe barrel.

In one embodiment, the fixture may be in the form of a sleeve that clamps or snaps onto the syringe barrel. Specifically, the sleeve may form an openly annular structure having a diameter that is defined by a relative position of a first edge and a second edge, both of which may be freely movable relative to each other. As a result, the sleeve may be flexed to install the sleeve on and remove the sleeve from the syringe barrel. Flexing the sleeve to move the first and second edges away from each other allows the sleeve to be clamped or snapped onto the syringe barrel or removed from the syringe barrel. When the sleeve is installed on the syringe, the first and second edges may be spaced, abutting, or overlapping, and the sleeve may extend around the entirety of or only part of the syringe barrel.

The data storage device may be separately attached to the sleeve in any appropriate manner, including adhering or otherwise anchoring the data storage device to an external surface of the sleeve. Alternatively, the data storage device may be incorporated into the structure of the sleeve itself. For example, in one embodiment, the data storage device may be embedded into the structure of the sleeve during the manufacturing process (e.g., an injection molding process).

In another embodiment, the fixture may be in the form of a band. In this embodiment, the band may extend about an entirety of the perimeter of the syringe barrel and include first and second edge portions that are disposed in overlapping relation when the band is installed on the syringe barrel. Similar to the sleeve embodiment discussed above, the data storage device may be separately attached to the band in any appropriate manner, including adhering or otherwise anchoring the data storage device to an external surface of the band. Alternatively, the data storage device may be incorporated into the structure of the band itself. For example, in one embodiment, the data storage device may be embedded into the structure of the band during the manufacturing process (e.g., an injection molding process).

To "semi-permanently" attach the fixture to the syringe barrel, the fixture may include at least one lock or latch. The lock may be of any appropriate size, shape, configuration, and/or type to detachably mount the fixture to the syringe barrel. When the lock is in a locked configuration, the fixture may not readily be removed from the syringe barrel (e.g., without proper tooling). In contrast, when the lock is in an unlocked configuration, the fixture may readily be removed from the syringe barrel. The lock may be engaged and disengaged in any appropriate manner, but in one embodiment, the fixture may be used in conjunction with an unlocking tool of any appropriate size, shape, configuration, and/or type to allow the unlocking tool to engage with the lock and change the lock from a locked configuration to an unlocked configuration.

For operator convenience and/or to avoid loss or misplacement of the unlocking tool, the unlocking tool may be detachably connected with the power injector in any appropriate manner (e.g., tethered, holstered, detachably fastened). In alternate or in addition, the unlocking tool may be integrated into the structure of the power injector in any appropriate manner. For example, in one embodiment, ejector pins may be incorporated into the power injector in any appropriate manner (e.g., actuated mechanically, electromechanically, hydraulically, pneumatically). The injection protocol may automate the use of the ejector pins and cause the ejector pins to engage with the lock at the termination of an injection procedure to change the lock from a locked configuration to an unlocked configuration. Operation of the ejector pins could be manually initiated as well.

A second aspect of the present invention is embodied by a method for delivering a medical fluid. This method includes loading a medical fluid into a medical container, mounting a data storage device on the medical container, and storing data on the data storage device. Thereafter, medical fluid may be discharged from the medical container before the data storage device is removed from the medical container (e.g., the data storage device may be removed from the medical container after the termination of an injection protocol). The data storage device may be removed from the medical container in a manner that allows the data storage device to be subsequently reused.

A number of feature refinements and additional features are applicable to the second aspect of the present invention. These feature refinements and additional features may be used individually or in any combination. As such, each of the following features that will be discussed may be, but are not required to be, used with any other feature or combination of features of the second aspect. The following discussion is applicable to the second aspect of the present invention.

The medical container may be any appropriate medical container for discharging medical fluid into a patient. For example, as discussed above with respect to the first aspect, the medical container may be in the form of a syringe of any appropriate size, shape, configuration, and/or type for use with a power injector, including a pre-filled syringe in which the syringe barrel is pre-filled at a first location with an appropriate medical fluid to be discharged by the power injector and transported in bulk to a second location in a common shipping container with other prefilled syringes.

A filling station of any appropriate size, shape, configuration, and/or type may be used to load the medical container with the medical fluid, and the medical fluid may include any appropriate fluid or combination of multiple fluids for loading into the medical container. The filling station may also include a read-write device operable to interface with a local network (e.g., a hospital and/or shipping or transportation system) to obtain, verify, and/or upload information related to an injection procedure, as well as write data to and/or read data from the data storage device (e.g., an RFID read-write device operable to communicate via radio signal with one or more data storage devices).

The data storage device may be of any appropriate construction including an RFID tag, a barcode, a magnetic stripe, and/or any other appropriate type of data storage technology. The read-write device of the filling station may be used to store on the data storage device fill data relating to the fluid loaded into the medical container (e.g., fluid type, concentration, manufacture date and/or lot, date filled, volume filled, expiration date, etc.) or relating to other relevant information such as patient identification or medical information or injection protocol information. Storing fill data on the data storage device may be an automated process initiated by the filling station, a manual or operator initiated process, or a combination of these options.

Mounting the data storage device onto the medical container may include attaching a fixture to the medical container. To facilitate the subsequent reuse of the data storage device, the fixture may be a reusable fixture that includes the data storage device. In this regard, the data storage device may be separately attached to the fixture in any appropriate manner (e.g., adhering or otherwise anchoring the data storage device to an external surface of the fixture) or the data storage device may be incorporated into the structure of the fixture itself (e.g., embedded into the structure of the fixture during a manufacturing process such as injection molding).

In one embodiment, mounting the data storage device onto the medical container may include latching the fixture onto the medical container. In this embodiment, removing the fixture from the medical container may include unlatching and/or detaching the fixture from the medical container before displacing the fixture from the medical container. Latching and unlatching/detaching the fixture may be executed manually, executed using a tool of any appropriate size, shape, configuration, and/or type, executed as part of an automated procedure, or executed through a combination of these options.

In another embodiment, mounting the data storage device onto the medical container may include locking the fixture onto the medical container. In this embodiment, removing the fixture from the medical container may include unlocking the fixture from the medical container before the fixture may be displaced from the medical container. The lock may be of any appropriate size, shape, configuration, and/or type to detachably mount the fixture to the medical container. When the lock is in a locked configuration, the fixture may not readily be removed from the medical container without appropriate tooling. In contrast, when the lock is in an unlocked configuration, the fixture may readily be removed from the medical container. The lock may be engaged and disengaged in any appropriate manner, but in one embodiment, unlocking or disengaging the lock may include operating a tool of any appropriate size, shape, configuration, and/or type to allow the tool to engage with the lock and change the lock from a locked configuration to an unlocked configuration. The step of unlocking the fixture may be executed manually, executed as part of an automated procedure, or executed through a combination of both.

Fluid may be discharged from the medical container in any appropriate manner. For instance, discharging fluid from the medical container may include installing the medical container onto and then operating a power injector of any appropriate size, shape, configuration, and/or type capable of discharging the medical fluid from the medical container into a patient.

In one embodiment, the power injector may also include a read-write device operable to read data from and/or write data to the data storage device. In this regard, the read-write device of the power injector may be used to read and verify the fill data stored on the data storage device to confirm the viability of the injection procedure. For example, the read-write device may read the data relating to concentration, expiration data, date filled, fill volume and verify the data as compared to a programmed injection protocol that the power injector is prepared to perform. If the data stored on the data storage device is inadequate, logic implemented in conjunction with the power injector and/or the read-write device may reject the use of the medical container. In addition, the read-write device may be used to store injection data (e.g., volume discharge, volume wasted) on the data storage device for subsequent reading and/or recording.

Notably, loading the medical fluid into the medical container, mounting the data storage device onto the medical container, storing data on the data storage device, discharging fluid from the medical container, and removing the data storage device from the medical container may occur at varying locations, as appropriate. For instance, medical fluid may be loaded into the medical container and discharged from the medical container at different locations. Specifically, the medical container may be loaded at the filling station located within a pharmacy, a pharmaceutical manufacturer, or any other appropriate pharmaceutical and/or medical distribution center before the medical container is transported from the filling station to a first location (e.g., an imaging room, a catheterization lab, a patient room) where the medical fluid may be discharged from the medical container into a patient.

As a result, and due to the reusable nature of the fixture, the data storage device may be transported from the first location back to the filling station for reuse. Once returned to the filling station, the data storage device may be cleared before the method discussed above is repeated using a second (e.g., new or resterilized) medical container and a second data set. That said, clearing the data from the data storage device and storing a second data set on the data storage device may collectively include overwriting the second data set to the data storage device. That is, clearing the data storage device and storing a second data set on the data storage device need not be two separate steps. In some instances, the second data set may simply be written or stored over any existing data on the data storage device.

In addition, the order in which the steps of method described above are executed may be altered such that they are completed at any appropriate time and in any appropriate order. For example, the filling station may load fluid into the medical container before, after, or while the data is being stored on the data storage device. Thus, loading medical fluid into the medical container and storing data on the data storage device may occur sequentially or in parallel. In another example, the data may be stored on the data storage device before or after the data storage device is mounted on the medical container. In yet another example, the data stored on the data storage device may be read prior to or while fluid is being discharged from the medical container. In a final example, the data storage device may be removed from the medical container before or after the data storage device is transported back to the filling station for reuse.

A number of feature refinements and additional features are separately applicable to each of the above-noted first and second aspects of the present invention. These feature refinements and additional features may be used individually or in any combination in relation to each of the above-noted first and second aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Finally, use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical).

Any "logic" that may be utilized by any of the various aspects of the present invention may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. This logic may be implemented at any single location or at multiple locations that are interconnected in any appropriate manner (e.g., via any type of network).

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any power injector may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one to embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

DETAILED DESCRIPTION

Figure 1:
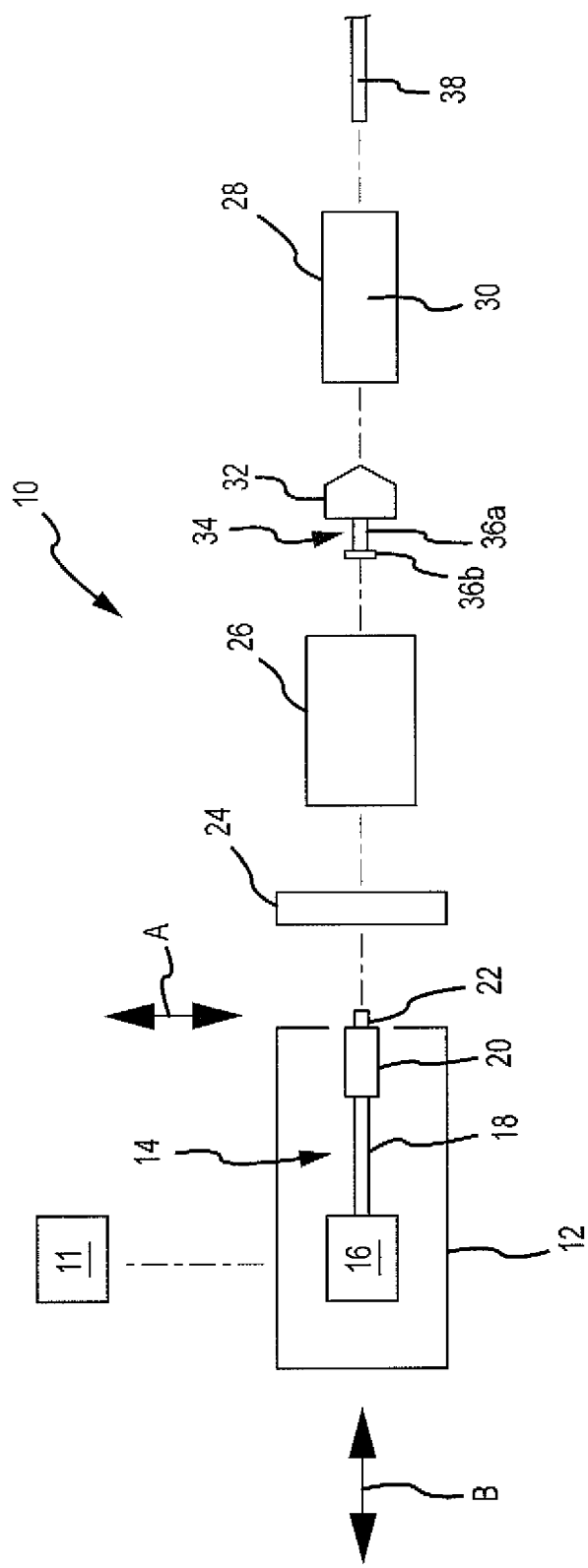
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
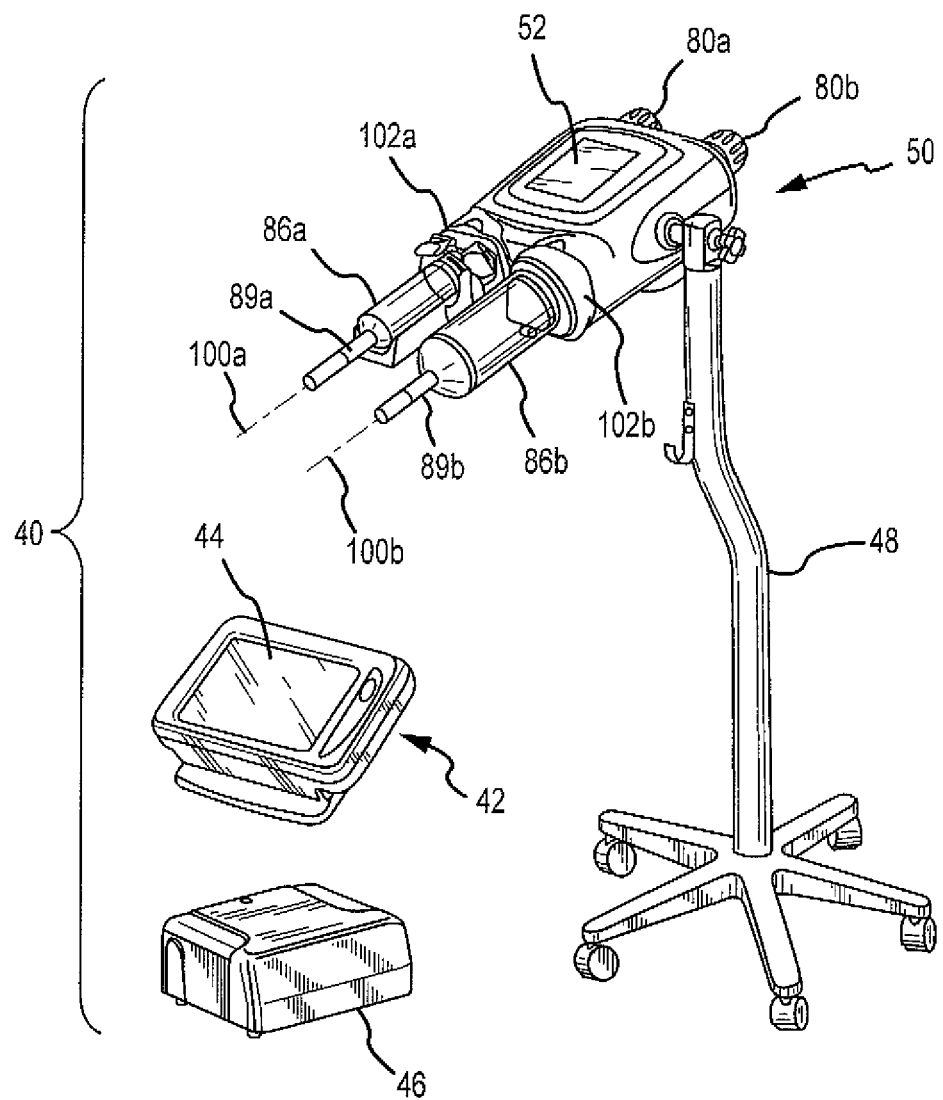
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
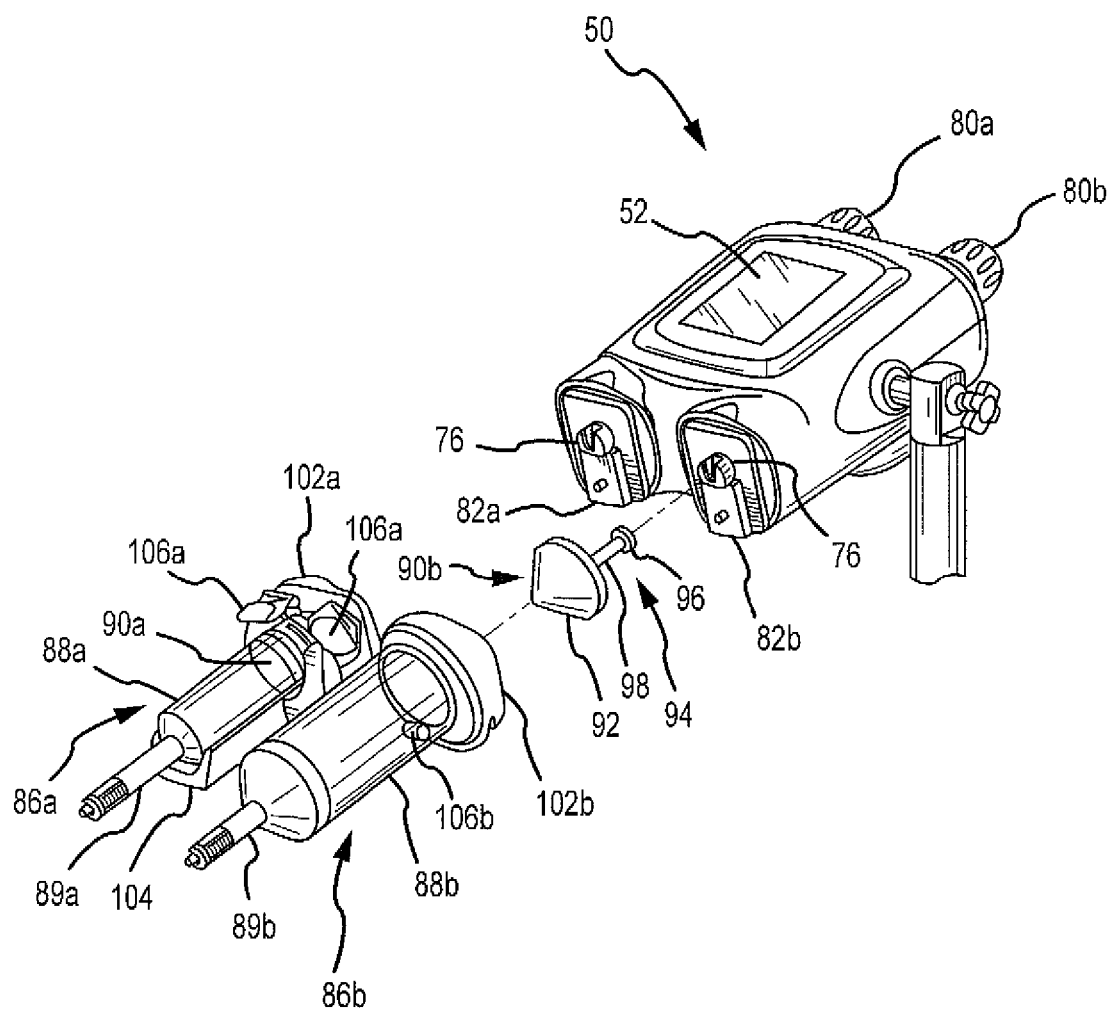
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50, The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
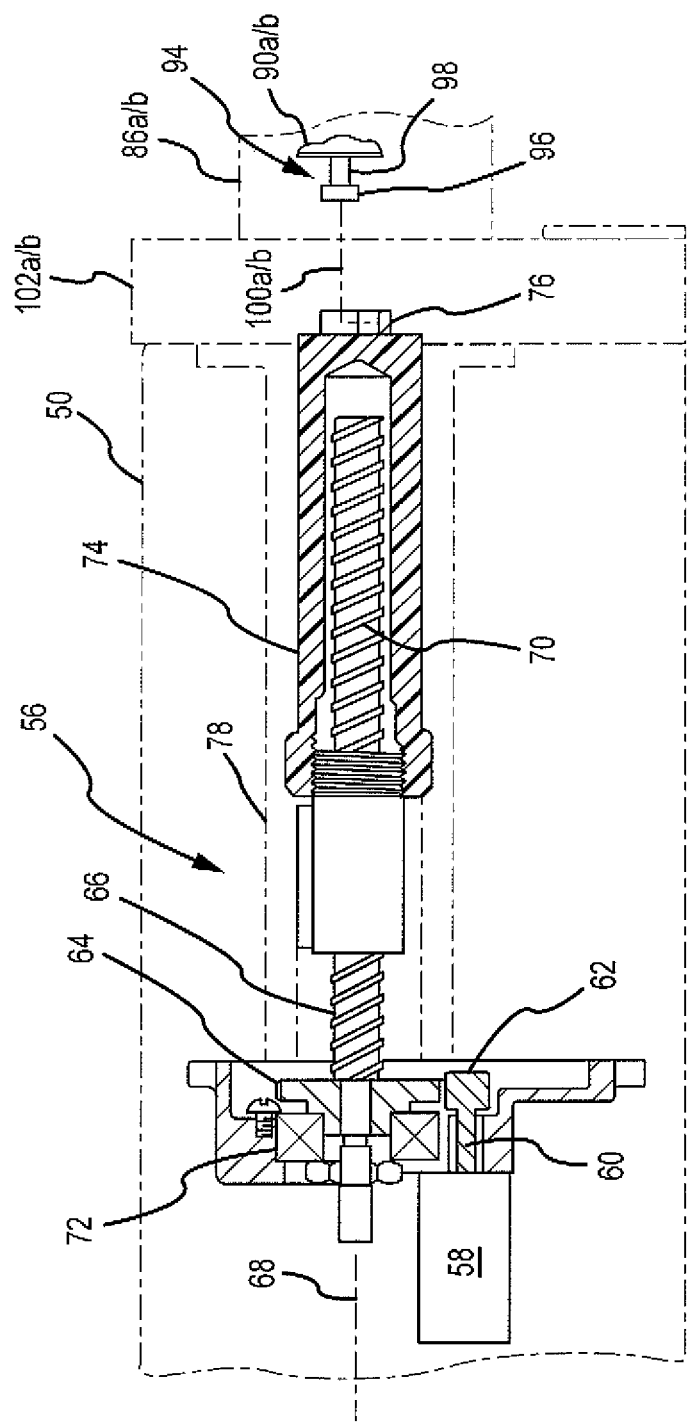
FIG. 2C is a schematic of one embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86*a/b* may be translated within a plane that is orthogonal to the axis 68 along which the ram 74 moves, This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3:
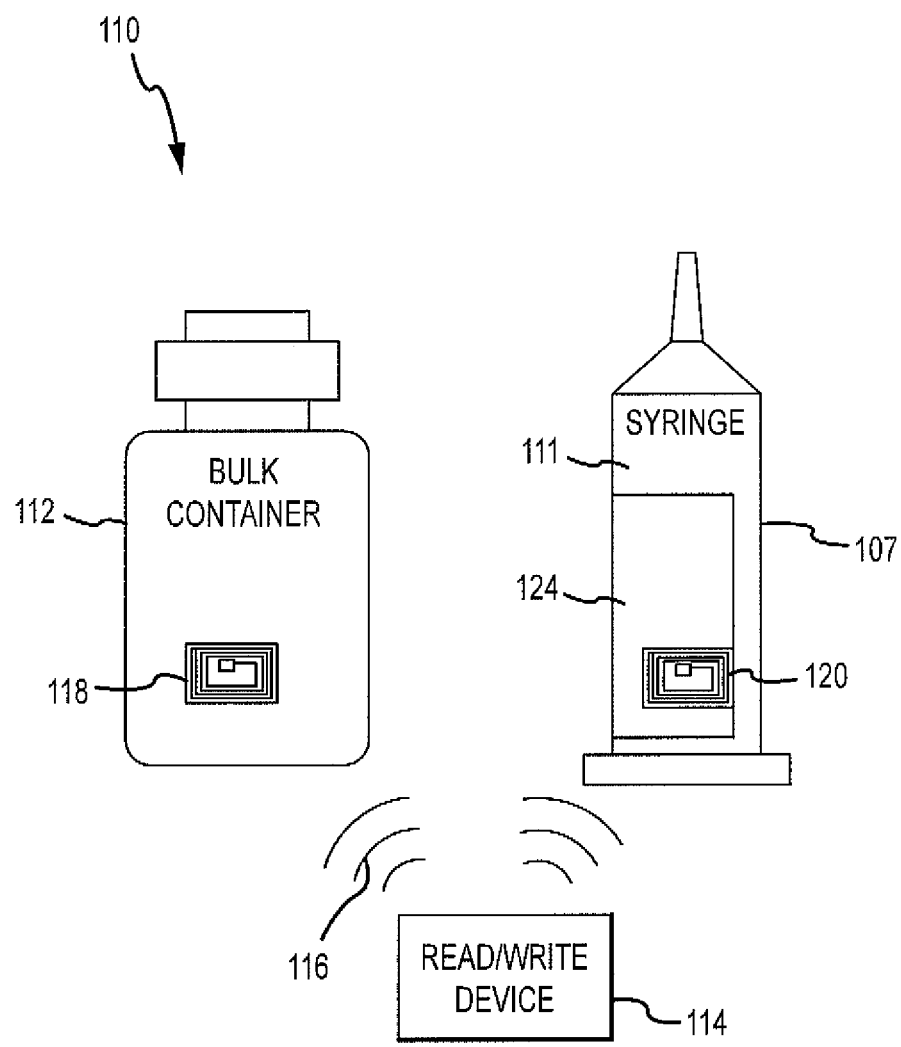
FIG. 3 is a schematic of one embodiment of a filling station for loading a power injector syringe with medical fluid.

FIG. 3 is a schematic of a filling station 110 for use in filling a medical container (e.g., a power injector syringe) for use with a power injection device (e.g., a power injector). The filling station 110 may be located within a pharmacy, at a pharmaceutical manufacturer, or in any other appropriate pharmaceutical and/or medical distribution center. Hereafter, the filling station 110 will be described in conjunction with a power injector syringe 107 for use with a power injector 108 (e.g., FIG. 4). The syringe 107 may be a medical container of any appropriate size, shape, configuration, and/or type, including, for instance, the syringes 28 (FIG. 1), 86 (FIGS. 2A-B) discussed above. The power injector 108 may be any power injector of an appropriate size, shape, type, or configuration, including, for instance, the power injectors 10 (FIG. 1), 40 (FIGS. 2A-C) discussed above. In addition, the power injector 108 may include a powerhead 109 of any appropriate size, shape, configuration, and/or type, including, for example, the powerheads 12 (FIG. 1), 50 (FIGS. 2A-B) discussed above.

Generally, the filling station 110 includes a bulk container/reservoir 112 that contains an appropriate medical fluid (e.g., contrast media, saline, fluid pharmaceuticals) for loading into the syringe 107. The filling station 110 may be configured to securely position the syringe 107 such that the filling station 110 may be used to fill the syringe 107 with an appropriate volume of fluid from the bulk container 112. One exemplary embodiment of a filling station that may be used to fill the syringe 107 is set forth in International Application Number PCT/US2004/017802.

In addition, the filling station 110 may include a read-write device 114. The read-write device 114 may be a radio frequency identification ("RFID") device operable to communicate via radio signal with one or more data storage devices (e.g., RFID tags, barcodes, magnetic stripes, and/or any other appropriate type of data storage technology) that may be associated with injecting fluids into a patient using the power injector 108. Accordingly, the read-write device 114 may be operable to read data from and/or write data to one or more data storage devices. The control electronics and/or logic associated with the read-write device 114 may be disposed in any appropriate location.

Reusable/rewritable data storage devices 118, 120 may be affixed to the bulk container 112 and the syringe 107, respectively. In this regard, FIG. 3 shows the syringe 107 with an attached fixture in the form of a sleeve 124 that will be discussed below in relation to FIG. 5. By way of initial summary, the sleeve 124 incorporates the data storage device 120 and is detachably mounted to the syringe 107 such that the sleeve 124 may be repeatedly attached to and removed from multiple syringes, including, for example, the syringes 107 (FIG. 3), 28 (FIG. 1), 86 (FIGS. 2A-B) discussed above.

At or around the time the syringe 107 is filled, the read-write device 114 may read data pertaining to the fluid within the bulk container 112 and, in turn, store relevant fill data (e.g., fluid type, concentration, manufacture date and/or lot, date filled, volume filled, expiration date, patient identification or medical information, injection protocol information) on the data storage device 120. The data storage device 120 may also designate the syringe status (e.g., that the syringe 107 remains unused or that fluid has not yet been discharged from the syringe 107). It should be appreciated that writing fill data to the data storage device 120 may be an automated process initiated by the filling station 110 during each fill procedure, a manual or operator-initiated process, or a combination of these options.

Figure 4:
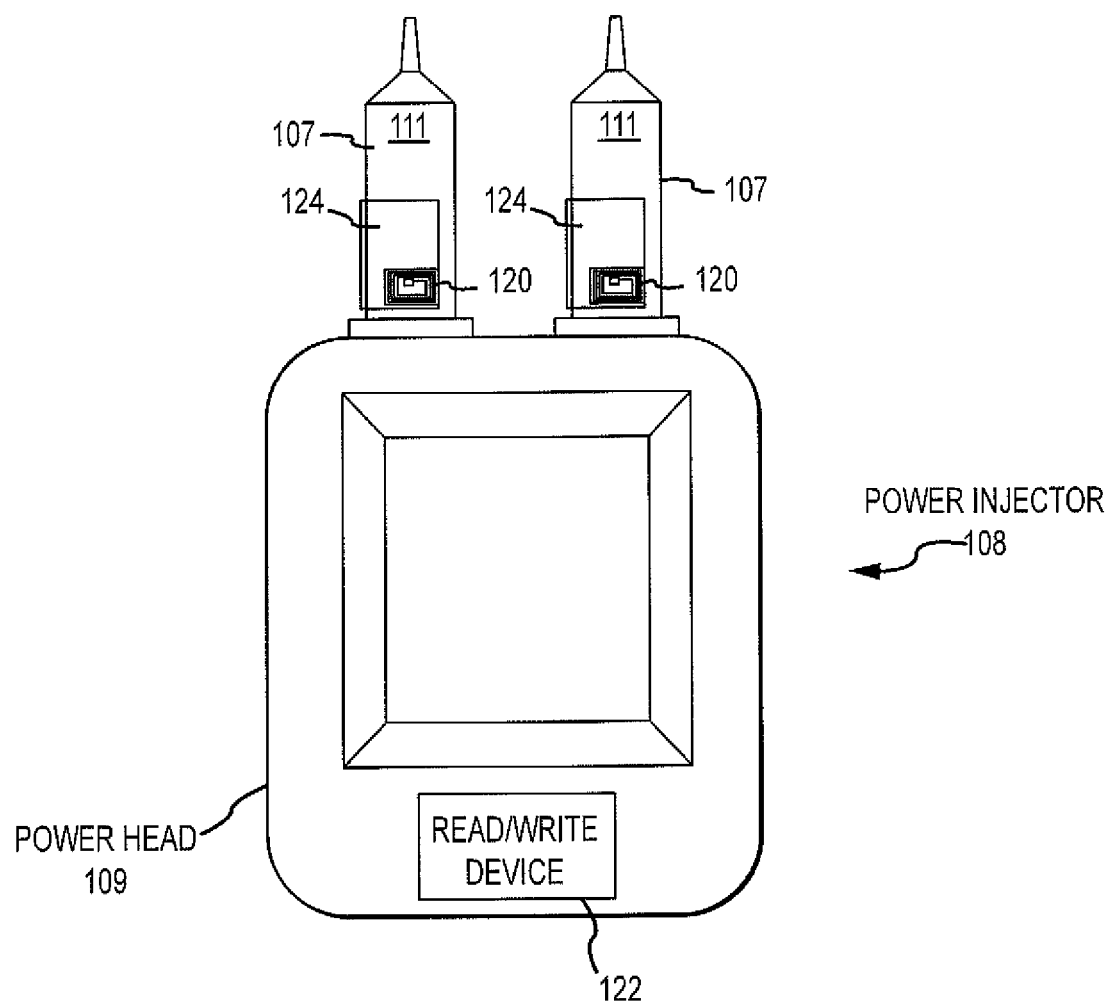
FIG. 4 is illustrates a top view of one embodiment of a dual-head configuration power injector with two installed power injector syringes.

Once filled, the syringe 107 may be transported to a first location or end-use site (e.g., an imaging room, catheterization lab, patient room) where the syringe 107 may be installed on the power injector 108, as shown in FIG. 4. The power injector 108 may include an additional read-write device 122. The read-write device 122 may be operable to read the fill data from the data storage device 120 on the syringe 107, thereby allowing the fill data to be verified against the programmed injection protocol that the power injector 108 is preparing to perform. The read-write device 122 may also be operable to store injection data relating to the current injection procedure (e.g., volume used, volume wasted, concentration injected, patient information, indication that fluid has been discharged from the syringe 107) on the data storage device 120 for later reading and/or recording at the filling station 110.

Because power injector syringes are generally disposed of after a single injection procedure, and because data storage devices may be rewritten and/or modified, the data storage device 120 may be incorporated within or separately attached to a fixture that detachably connects to the syringe 107, as discussed above. The fixture may be attached to the syringe 107 at the filling station 110 at or around the time the syringe 107 is loaded with medical fluid, and the fixture may be removed from the syringe 107 at some time after the power injector 108 has discharged the syringe 107 at the end-use site. Incorporating the data storage device 120 into the fixture in this manner allows the fixture, and thus the data storage device 120, to be used again and again with different syringes for repeated injection procedures.

Figure 5:
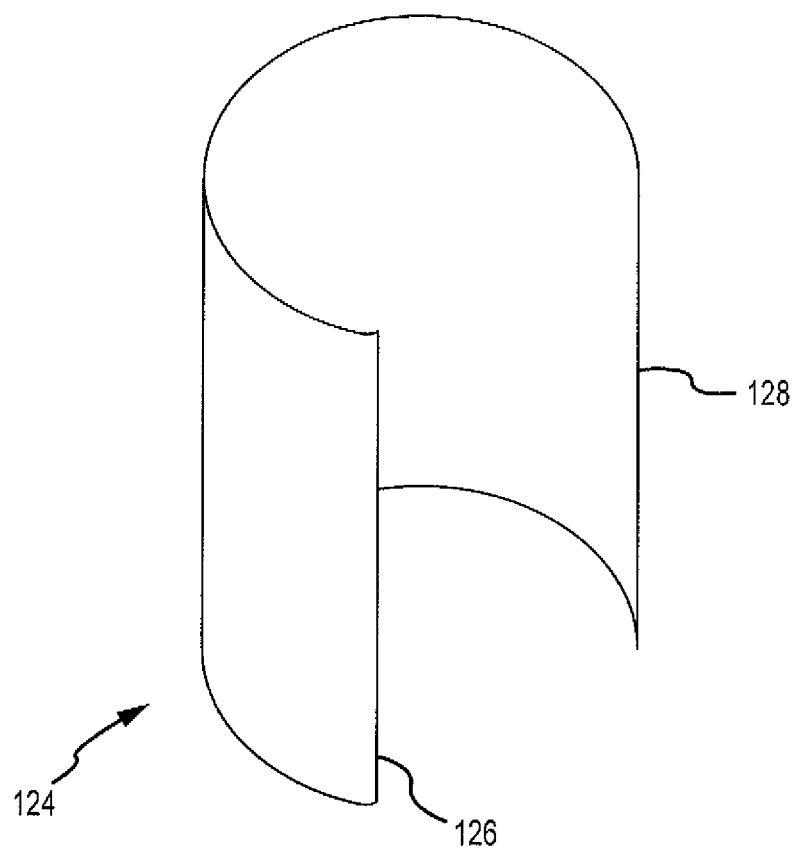
FIG. 5 illustrates one embodiment of a fixture for attachment to a power injector syringe, where the fixture includes a data storage device.

FIG. 5 illustrates one embodiment of a fixture for attachment to the syringe 107. In this embodiment, the fixture is in the form of a sleeve 124. The data storage device 120 may be separately attached to the sleeve 124 or it may be integrated or incorporated directly into the structure of the sleeve 124. As shown in FIG. 5, the sleeve 124 may be in the form of a semi-cylindrical structure having a first edge 126 and a second edge 128. The sleeve 124 is configured such that the first and second edges 126, 128 may move freely relative to each other (e.g., by a flexing of the sleeve 124), thereby allowing an operator to separate the first and second edges 126, 128 and clamp or snap the sleeve 124 onto and off of a barrel 111 of the syringe 107. When the sleeve 124 is attached to the syringe 107, as shown in FIG. 4, the first and second edges 126, 128 may be spaced, abutting, or overlapping. In other words, the sleeve 124 may extend around the entirety of or only part of the syringe barrel 111. When mounted on the barrel 111 of the syringe 107, the sleeve 124 may exert a compressive force on the barrel 111, for instance based upon the elasticity of the sleeve 124.

FIGS. 6A-B through 7A-B illustrate another embodiment of a fixture for detachably mounting a data storage device 120 to a syringe 107. In this embodiment, the fixture is in the form of a circular band 130 that extends about an entire perimeter of the syringe barrel 111. The band 130 includes a first edge portion 142 and a second edge portion 144. The first and second edge portions 142, 144 are disposed in overlapping relation when the band 130 is positioned about the syringe barrel 111. Therefore, the band 130 extends about the entire circumference of the syringe barrel 111.

Figure 6A:
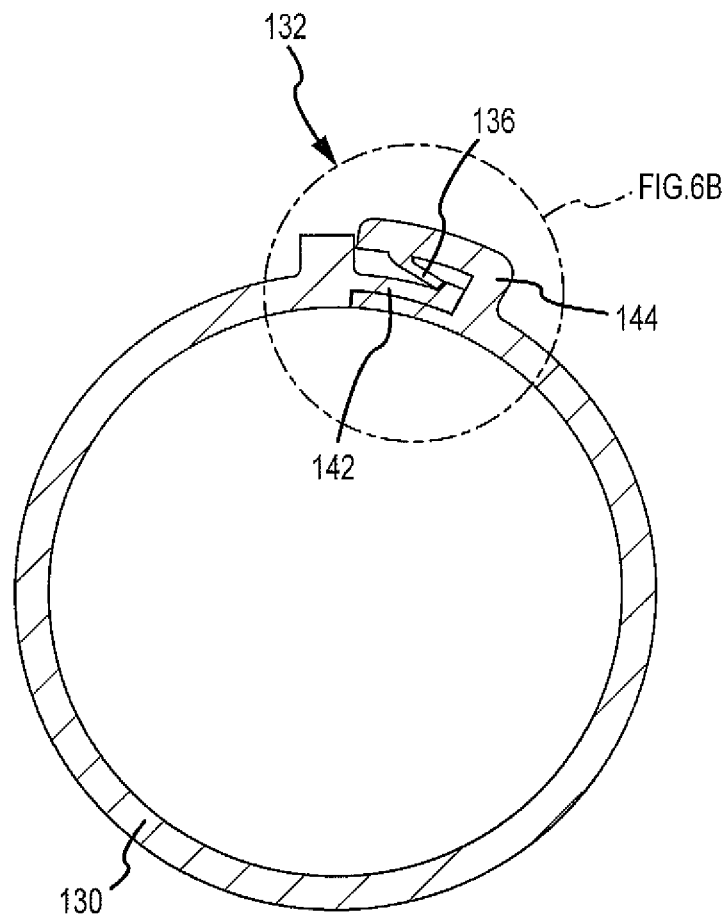
FIG. 6A illustrates a cross-sectional view of another embodiment of a fixture that includes a data storage device for attachment to a power injector syringe.
Figure 6B:
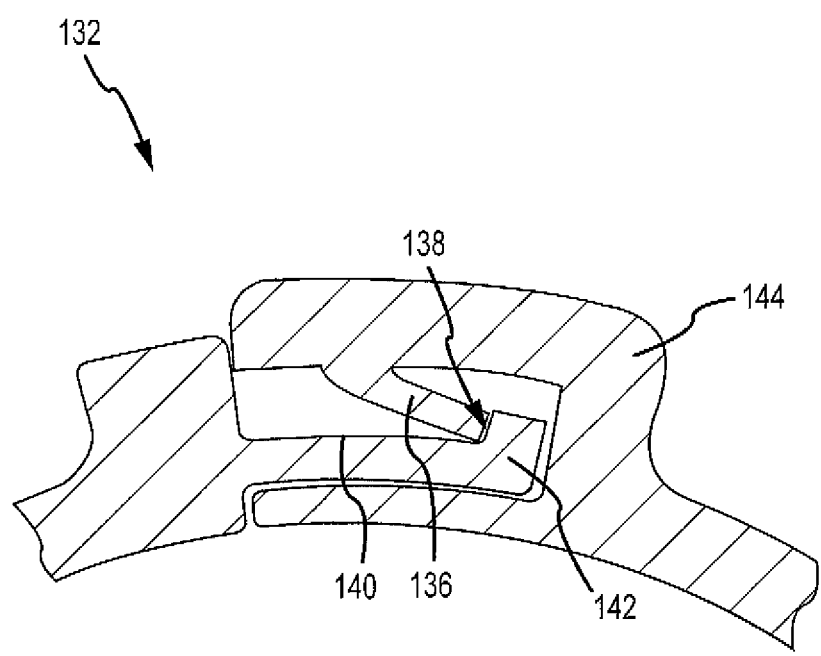
FIG. 6B illustrates a detailed view of a lock for the fixture of FIG. 6A.

The first and second edge portions 142, 144 also form a lock that detachably mounts the band 130 to the syringe barrel 111. Specifically, when in a locked configuration, a tab 136 extends from the second edge portion 144 and wedges against a sidewall 138 that forms part of a notch 140 in the first edge portion 142, as shown in FIGS. 6A-B. The tab 136 may be biased to a locking position (e.g., by being at least somewhat elastically deformable or deflectable).

Figure 7A:
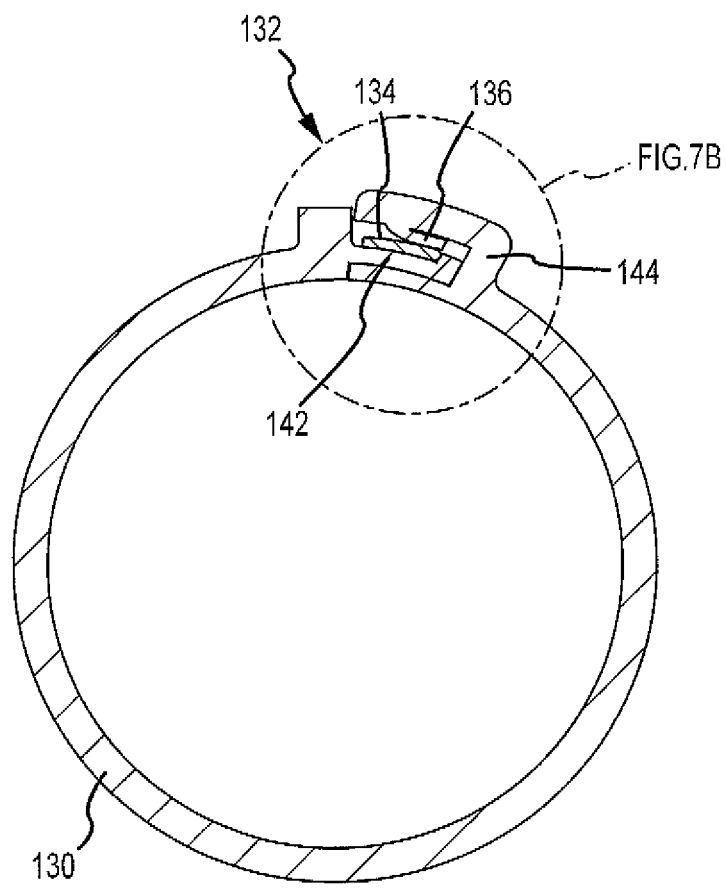
FIG. 7A illustrates a cross-sectional view of the fixture of FIG. 6A with an unlocking tool engaged with the lock detailed in FIG. 6B.
Figure 7B:
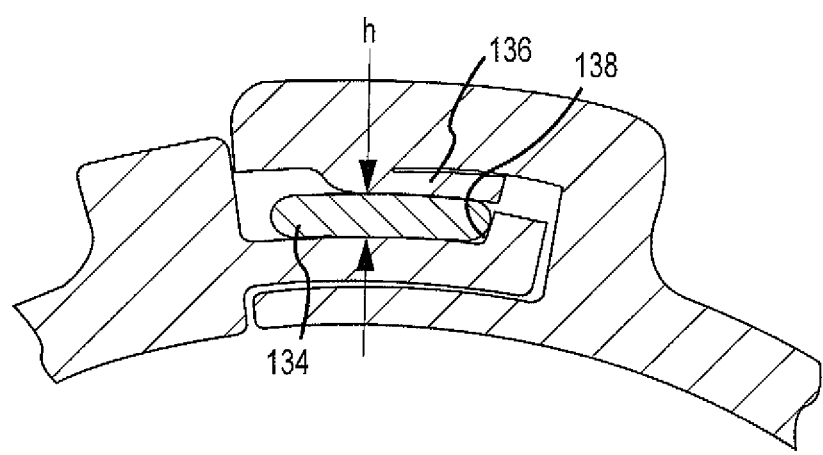
FIG. 7B illustrates a detailed view of the unlocking tool of FIG. 7A engaged with the lock detailed in FIG. 6B.

The band 130 may be removed from the syringe 111, and thereafter may be mounted on another syringe. In this regard, a tool 134 may be inserted into the notch 140, such that it deflects the tab 136 out of the notch 140 and releases the first and second edge portions 142, 144, as shown in FIGS. 7A-B. Once the first and second edge portions 142, 144 are released, they may be separated a distance sufficient to allow the band 130 to be attached to or removed from the syringe barrel 111 (e.g., by flexing the band 130). Because the tab 136 may be biased to the locked position, as discussed above, the tab 136 may automatically recover to the locked position after the band 130 is unlocked and any restraining force from the tool 134 is removed.

The tool 134 may be a wedge-like device having a height (h) that is at least equal to the height of the sidewall 138 and that is configured to slide within the notch 140 and displace the tab 136 out of the notch 140, thereby releasing the first and second end portions 142. However, the tool 134 may be of any appropriate size, shape, configuration and/or type.

Generally, it may be desirable to avoid having the band 130 be removable from the syringe 107 without the use of a tool of some sort.

Figure 8:
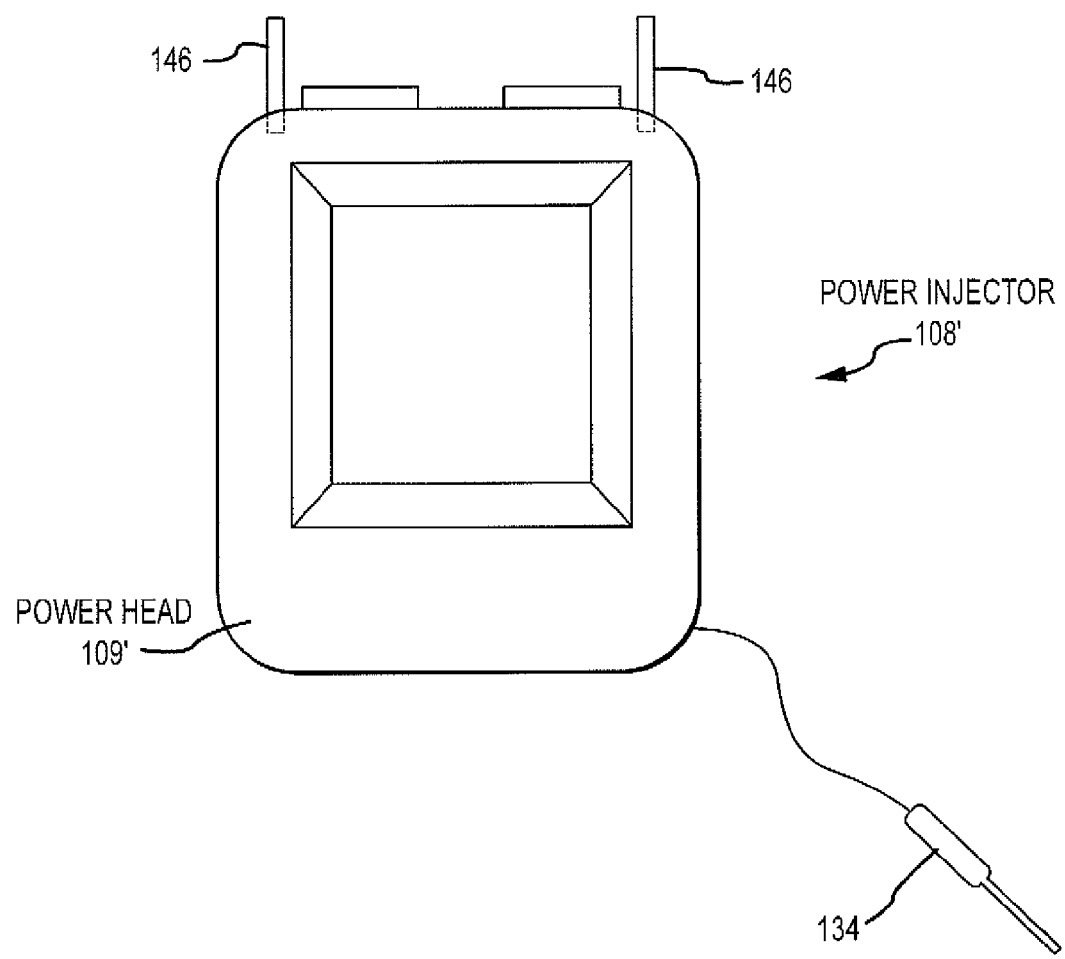
FIG. 8 illustrates a top view of one embodiment of a dual-head configuration power injector with two integrated ejector pins and a tethered unlocking tool.

For operator convenience, as well as to avoid misplacement of the tool 134, the tool 134 may be detachably mounted to any appropriate part the power injector 108 that allows the tool 134 to be removed from the power injector 108 and stored again in any appropriate manner. In this regard, FIG. 8 illustrates the tool 134 being tethered to a variation of power injector 108' having a powerhead 109'. Alternately, the tool 134 may be integrated directly into the power injector 108'. For example, in one embodiment also shown in FIG. 8, the power injector 108' may include an appropriate number of ejector pins 146. Each ejector pin 146 may be appropriately configured such that when actuated after the termination of an injection procedure, the pin 146 drives forward into the notch 140 of the band 130, thereby displacing the tab 136 and releasing the first and second edge portions 142, 144 to allow the band 130 to be removed from the syringe barrel 111. The ejector pins 146 may be of any appropriate size, shape, configuration and/or type and may be actuated in any appropriate manner known in the art (e.g., mechanical, electromechanical, pneumatic, hydraulic, etc.). It should be understood that the power injector 108' may include one or both of the tooling options discussed above. That is, the power injector 108' may include a detachably mounted tool, an integrated tool, or both.

In general and as discussed with respect to FIG. 1, some injection procedures may result in a relatively high pressure being generated within the syringe. In this regard, a syringe is sometimes disposed within a pressure jacket that protects the syringe from rupturing under pressure. The pressure jacket is typically associated with the powerhead of the power injector in a manner that allows a syringe to be disposed therein as a part of or after the process of installing the syringe on the powerhead. In this regard, the sleeve 124 (FIG. 5) and the band 130 (FIGS. 6A-B and 7A-B) may function in a secondary capacity as pressure sleeves. That is, when attached to the syringe 107, the sleeve 124 (FIG. 5) and the band 130 (FIGS. 6A-B and 7A-B) may each form a structural member about the syringe 107. As such, the sleeve 124 (FIG. 5) and the band 130 (FIGS. 6A-B and 7A-B) may be used as appropriate to both interface between the powerhead 109 and the syringe 107 and to structurally support the syringe 107 when subjected to high pressures during an injection procedure.

Figure 9:
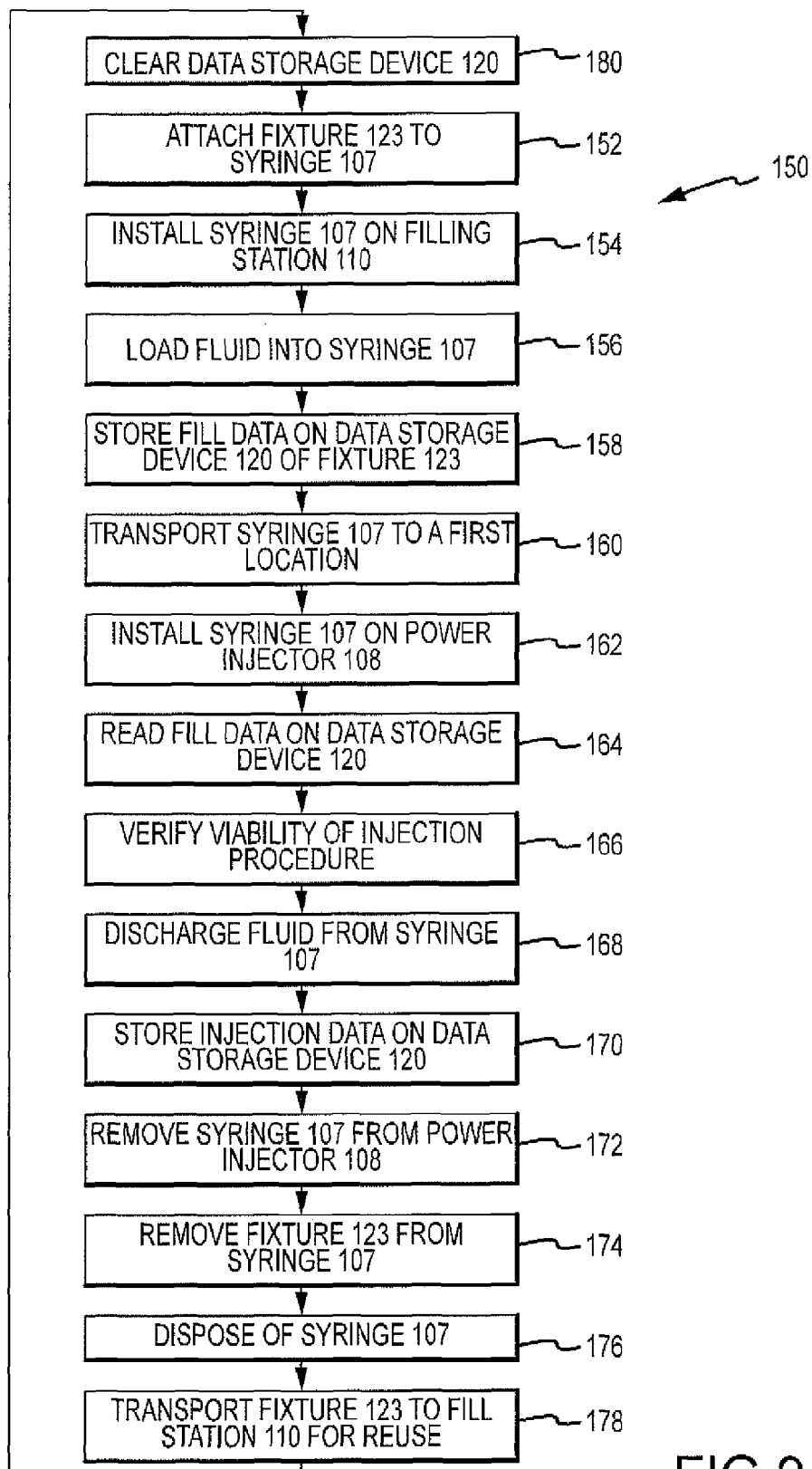
FIG. 9 is a flowchart for a method of delivering medical fluid using a fixture having a data storage device.

FIG. 9 is a flowchart of a method 150 for delivering a medical fluid to a patient using a fixture 123. The fixture 123 may be of any appropriate size, shape, configuration, and/or type, including, for instance, the sleeve 124 (FIG. 5) or the band 130 (FIGS. 6A-B and 7A-B) discussed above. When using a new fixture 123, a first step 152 of the method 150 may be to attach the fixture 123 containing the data storage device 120 to the syringe 107. As discussed above, the syringe 107 may be any appropriate medical container, including, for example, the syringes 28 (FIG. 1), 86 (FIGS. 2A-B) or any other appropriate medical container for use with a power injector 108. If the sleeve 124 is utilized, the step 152 of attaching the fixture 123 to the medical container may include separating the first and second edges 126, 128 and snapping the sleeve 124 about the syringe barrel 111 of the syringe 107. if the band 130 is utilized, the step 152 of attaching the fixture 123 to the syringe 107 may include using the tool 134 to unlock the band 130 before separating the first and second edge portions 142, 144 and disposing the band 130 about the syringe barrel 111 of the syringe 107, as discussed above.

The next step 154 of the method 150 may be to install the syringe 107 on a filling station such as, for example, the filling station 110 discussed above. Installing the syringe 107 on the filling station 110 may include interconnecting the syringe 107 with the bulk container 112 of the filling station 110 in a position that is within the field of view of the read-write device 114 of the filling station 110, thereby allowing the read-write device 114 to communicate with the data storage device 120 of the fixture 123.

Once the syringe 107 is installed on the filling station 110, the next step 156 may be to load fluid into the syringe 107. The method 150 may then proceed to step 158, in which the read-write device 114 of the filling station 110 stores the relevant fill data to the data storage device 120. It should be appreciated that the order of steps 154, 156, and 158 may be altered. In other words, these steps may be completed in any appropriate order that is consistent with a preferred institutional protocol, process, or procedure. For example, loading fluid into the syringe 107 and storing fill data to the data storage device 120 may be completed in parallel. In another example, storing fill data to the data storage device 120 may be completed prior to installing the syringe 107 on the filling station 110.

The next step 160 of the method 150 may be to transport the filled syringe 107 and the attached fixture 123 to a first location, which, as discussed above, may include an end-use site such as an imaging room, a catheterization lab, a patient room or the like. Transporting the syringe 107 may be completed in any appropriate manner, including, for example, a mail or courier service, personal delivery, or an automated hospital distribution system.

Once at the end-use site, the method 150 may proceed to step 162. In the execution of step 162, the syringe 107 may be installed on the power injector 108 or any other appropriate power injector (e.g., the power injector 10 of FIG. 1, the power injector 40 of FIGS. 2A-C). Installing the syringe 107 on the power injector 108 may include interconnecting a plunger (not shown) of the syringe 107 to a syringe plunger driver assembly such as, for example, the syringe plunger driver assembly 56 (FIG. 20). Once connected, the power injector 108 may be operable to drive (e.g., advance and/or retract) the plunger of the syringe 107. Step 162 may also include interconnecting any appropriate disposables such as a tubing set to the syringe 107.

Once the syringe 107 is installed on the power injector 108, the next step 164 of the method 150 may be for the read-write device 122 of the power injector 108 to read the fill data stored on the data storage device 120. In this regard, the syringe 107 may be installed onto the power injector 108 such that the data storage device 120 of the fixture 123 is within the field of view of the RFID read-write device 122 of the power injector 108.

Once the fill data from the data storage device 120 has been read, the next step 166 may be to verify the viability of the injection protocol programmed on the power injector 108 as compared to the fill data stored on the data storage device 120. This verification may take the form of comparing the fill data to a programmed injection protocol to confirm, for example, that the syringe 107 is unused (i.e., that the syringe 107 has not yet been discharged into a patient), that the fluid contained within the syringe 107 is not expired, that the syringe 107 contains fluid in the correct concentration and volume, that the patient identification information is correct, or to confirm any other relevant fill data stored on the data storage device 120 at the filling station 110.

Verifying the viability of the injection procedure may be performed in a variety of ways. For example, the operator may review the fill data and confirm that the injection procedure is viable, or alternatively, logic implemented in conjunction with the power injector 108 and/or the read-write device 122 may automatically compare the fill data stored on the data storage device 120 with information obtained from other data storage devices (e.g., a data storage device disposed or incorporated within a patient identification bracelet or an operator identification badge) or the programmed injection protocol that the power injector 108 is prepared to perform. Verification may reduce the potential of costly and/or dangerous mistakes in the injection procedure, including, for example, injecting the wrong fluid into a patient, injecting an expired fluid into a patient, using the wrong protocol for a particular patient and/or syringe, injecting a used or empty syringe into a patient.

Once the viability of the injection procedure has been verified, the method 150 may proceed to step 168. The execution of step 168 may include using the power injector 108 to discharge fluid from the syringe 107 into a patient according to the programmed injection protocol. At or around the same time, the read-write device 122 of the power injector 108 may complete the next step 170 of storing injection data on the data storage device 120 for subsequent reading and/or recording. Such injection data may include the volume used, the volume wasted, a designation that the syringe 107 has been used (e.g., that fluid has been discharged from the syringe 107), and/or any other appropriate injection data.

Notably, discharging fluid from the syringe 107 and storing injection data on the data storage device 120 may be completed in any appropriate order that is consistent with a preferred institutional process or procedure. For example, discharging fluid from the syringe 107 and storing injection data to the data storage device 120 may be completed in parallel, or alternatively, storing injection data to the data storage device 120 may be completed before fluid is discharged from the syringe 107.

In addition, it should be appreciated that the fill data stored on the data storage device 120 at the filling station 110 and the injection data stored on the data storage device 120 at the power injector 108, along with any other information described herein that is stored onto the data storage device 120 or read by read-write devices 114, 122, may be used for purposes beyond the injection process. For example, such information may be used to track inventories, billing, equipment performance, patient injection history, and/or operator activity. During the method 150, the read-write devices 114, 122 may also interface with a local network (e.g., a hospital and/or shipping or transportation system) to obtain, verify and/or upload relevant information.

The next step 172 may be to remove the syringe 107 from the power injector 108, followed by the step 174 of removing the fixture 123 from the used syringe 107. The steps 172 and 174 may be executed manually, executed as part of an automated process, or executed as a combination of both the manual and automated options. For example, in instances in which the band 130 (FIGS. 6A-B and 7A-B) is locked about the syringe barrel 111 of the syringe 107, the step 174 of removing the fixture 123 from the syringe 107 may include the operator using the handheld tool 134 to unlock the lock 132, as discussed above. Alternatively, the power injector 108 may automatically employ an unlocking mechanism (e.g., the injector pin or pins 146 shown in FIG. 8) to unlock the band 130 at the termination of the injection procedure. Moreover, an operator may manually remove the syringe 107 from the power injector 108 or the power injector 108 may automatically eject the syringe 107 at the termination of the injection procedure.

After the fixture 123 has been removed, the method may proceed to step 176, which may include disposing of the used syringe 107 in any appropriate manner. Alternatively, in some limited instances, the step 176 may involve resterilizing the syringe 107 for reuse.

The next step 178 may include transporting the fixture 123 back to the filling station 110 for reuse with a new syringe 107. Transporting the fixture 123 back to the filling station 110 may be completed in any appropriate manner, including, for example, a mail or courier service, personal delivery, or an automated hospital medication distribution system, etc. It should also be appreciated that removing the fixture 123 from the used syringe 107, disposing of the used syringe 107, and transporting the fixture 123 back to the filling station 110 for reuse with a new syringe 107 may be completed in any appropriate order consistent with the institutional protocol, practice, or procedure. For example, the fixture 123 may remain attached to the syringe 107 as it is transported back to the filling station 110, where the fixture 123 may be removed from the syringe 107 before the syringe 107 is disposed of or sent for resterilization. Because the fixture 123 includes the data storage device 120, which denotes that the attached syringe 107 has been used, leaving the fixture 123 in place on the syringe 107 until the fixture 123 is returned to the filling station 110 may help to avoid the risk of mistakenly reusing the attached syringe 107 (e.g., using the power injector 108 at the end-use site to discharge an empty syringe 107 into the same patient or discharging the used syringe 107 into another patient).

Once the fixture 123 has been transported back to the filling station 110, the next step 180 of the method 150 may involve using the read-write device 114 of the filling station 110 to clear the data storage device 120 before the fixture 123 is attached to a second syringe 107 for another injection procedure. It should be appreciated that clearing the data storage device 120 may be a separate and distinct step of method 150 or it may be subsumed within the step 158 of storing a second fill data set to the data storage device 120. That is, the read-write device 114 of the filling station 110 may simply overwrite the first fill data set with a second fill data set for a new injection procedure, thereby obviating the need to separately clear the data storage device 120. Another option would be to clear the data storage device 120 as part of the removal of the fixture 123 from a syringe-removal the fixture 123 could automatically result in a clearing of the associated data storage device 120.

The logic for the read-write devices 114, 122 may be implemented in any appropriate manner, including, without limitation, in any appropriate software, firmware, or hardware, using one or more platforms, using one or more processors, using memory of any appropriate type, using any single computer of any appropriate type or multiple computers of any appropriate type and interconnected in any appropriate manner, or any combination thereof. Moreover, the logic for the RFID read-write devices 114, 122 may be implemented at any single location or at multiple locations that are interconnected in any appropriate manner (e.g., via any type of network).

Based upon the foregoing, the fixture 123 is subject to a number of characterizations, which may apply individually or in any combination: 1) the fixture 123 may be characterized as being detachably mounted to a syringe 107; 2) the fixture 123 may be characterized as being separately installable on each of a plurality of syringes 107—the fixture 123 may be installed on one syringe 107, removed from this syringe 107, and then installed on another syringe 107; and 3) the fixture 123 may be characterized as including a connective structure, where this connective structure is of a configuration that allows the fixture 123 to be installed on a syringe 107, and where this connective structure is of a configuration so as to remain in tact when the fixture 123 is removed from one syringe 107 such that the fixture 123 may be installed on a different syringe 107 using this same connective structure.

The foregoing description has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A power injector syringe assembly, comprising:
   a syringe barrel;
   a plunger movable relative to said syringe barrel and comprising a plunger head disposed within said syringe barrel;
   a fixture detachably mounted on said syringe barrel, wherein said fixture is a band which in turn comprises first and second edge portions that are movable relative to each other and that cooperate to define a lock when said band is installed on said syringe barrel, wherein said first edge portion of said band comprises a sidewall that forms a notch, wherein said second edge portion of said band comprises an outer wall and an inner wall that are separated from one another by an open space and with said inner wall of said second edge portion being located between said syringe barrel and said outer wall of said second edge portion, wherein said first edge portion of said band extends into said open space of said second edge portion of said band, wherein said second edge portion of said band further comprises a tab that extends from said outer wall in the direction of said inner wall to engage said sidewall of said first edge potion to define a locked configuration for said band, and wherein said band is flexible to accommodate flexure of said band to increase a spacing between said first and second edge portions, to in turn accommodate both installation and removal of said band relative to said syringe barrel; and
   a data storage device on said band, wherein said fixture is on said syringe barrel prior to installing said syringe barrel on a power injector.

2. The power injector syringe assembly of claim 1, wherein said syringe barrel and said plunger comprise a pre-filled syringe, and wherein said pre-filled syringe comprises medical fluid within said syringe barrel.

3. The power injector syringe assembly of claim 1, wherein said tab is elastically deformable or deflectable to bias said tab against said sidewall.

4. The power injector syringe assembly of claim 1, further comprising an unlocking tool that is engageable with said lock to change said lock from said locked configuration to an unlocked configuration, wherein said band is removable from said syringe barrel with said lock being in said unlocked configuration.

5. The power injector syringe assembly of claim 1, wherein said band extends along an entirety of a perimeter of said syringe barrel.

6. The power injector syringe assembly of claim 1, wherein said data storage device comprises a radio frequency identification tag.

7. The power injector syringe assembly of claim 1, wherein said data storage device comprises a data structure that comprises stored data, which in turn comprises at least one of a syringe status, fluid type, concentration, manufacture date, lot, date filled, volume filled, expiration date, patient identification information, patient medical information, or injection protocol information.

8. The power injector syringe assembly of claim 1, wherein said data storage device is separately attached to said band.

9. The power injector syringe assembly of claim 1, wherein said data storage device is incorporated into the structure of said band.

10. A power injector syringe assembly, comprising:
a syringe barrel;
a plunger movable relative to said syringe barrel and comprising a plunger head disposed within said syringe barrel;
a fixture detachably mounted on said syringe barrel, wherein said fixture is a sleeve which in turn comprises first and second edges that at all times remain freely movable relative to each other by said sleeve excluding the ability to latch said first edge relative to said second edge, wherein said sleeve is an elastic structure, wherein said sleeve is configured to be flexed into a first configuration to increase a spacing between said first and second edges, to in turn accommodate both installation and removal of said sleeve relative to said syringe barrel, and wherein said sleeve is configured to assume a second configuration when installed on said syringe barrel where said sleeve exerts a compressive force against said syringe barrel; and
a data storage device on said sleeve, wherein said fixture is on said syringe barrel prior to installing said syringe barrel on a power injector.

11. The power injector syringe assembly of claim 10, wherein said syringe barrel and said plunger comprise a pre-filled syringe, and wherein said pre-filled syringe comprises medical fluid within said syringe barrel.

12. The power injector syringe assembly of claim 10, wherein said first and second edges are separated from one another by a gap when said sleeve is installed on said syringe barrel.

13. The power injector syringe assembly of claim 10, wherein said first and second edges are disposed in abutting relation when said sleeve is installed on said syringe barrel.

14. The power injector syringe assembly of claim 10, wherein said sleeve further comprises first and second edge portions that are disposed in overlapping relation when said sleeve is installed on said syringe barrel, wherein said first edge portion comprises said first edge and said second edge portion comprises said second edge.

15. The power injector syringe assembly of claim 10, wherein said data storage device comprises a radio frequency identification tag.

16. The power injector syringe assembly of claim 10, wherein said data storage device comprises a data structure that comprises stored data, which in turn comprises at least one of a syringe status, fluid type, concentration, manufacture date, lot, date filled, volume filled, expiration date, patient identification information, patient medical information, or injection protocol information.

17. The power injector syringe assembly of claim 10, wherein said data storage device is separately attached to said sleeve.

18. The power injector syringe assembly of claim 10, wherein said data storage device is incorporated into the structure of said sleeve.

19. A system, comprising:
a power injector comprising a power injector syringe assembly which in turn comprises:
a syringe barrel;
a plunger movable relative to said syringe barrel and comprising a plunger head disposed within said syringe barrel;
a fixture detachably mounted on said syringe barrel, wherein said fixture is a band which in turn comprises first and second edge portions that are movable relative to each other and that cooperate to define a lock when said band is installed on said syringe barrel, wherein said band is flexible to accommodate flexure of said band to increase a spacing between said first and second edge portions, to in turn accommodate both installation and removal of said band relative to said syringe barrel;
a data storage device on said band, wherein said fixture is on said syringe barrel prior to installing said syringe barrel on said power injector;
an unlocking tool that is engageable with said lock to change said lock from said locked configuration to an unlocked configuration, wherein said unlocking tool is one of detachably connected with said power injector or integrated into the structure of said power injector, and wherein said band is removable from said syringe barrel with said lock being in said unlocked configuration.

20. The system of claim 19, wherein said first edge portion comprises a sidewall that forms a notch, wherein said second edge portion comprises a tab that wedges against said sidewall when said lock is in in said locked configuration, and wherein said unlocking tool has a height that is at least equal to a height of said sidewall and that is configured to slide within said notch and displace said tab out of said notch to dispose said lock in an unlocked configuration.

21. The system of claim 19, wherein said unlocking tool is detachably mounted to the power injector by a tether.

22. The system of claim 19, wherein said unlocking tool is integrated into the structure of the power injector, wherein said unlocking tool includes at least one ejector pin that is configured to drive forward to position said lock into said unlocked configuration of said lock.

23. The system of claim 22, wherein said first edge portion includes a sidewall that forms a notch, wherein said second edge portion includes a tab that wedges against the sidewall when in a locked configuration of the lock, and wherein said ejector pin is configured to drive forward into said notch to displace the tab from the sidewall and thereby position said lock in said unlocked configuration.

* * * * *